US005486457A

United States Patent [19]
Butler et al.

[11] Patent Number: 5,486,457
[45] Date of Patent: Jan. 23, 1996

[54] METHOD AND SYSTEM FOR MEASUREMENT OF MECHANICAL PROPERTIES OF MOLECULES AND CELLS

[75] Inventors: James P. Butler, Brookline; Jeffrey J. Fredberg, Sharon; Donald E. Ingber, Boston; Ning Wang, Brookline, all of Mass.

[73] Assignees: Children's Medical Center Corporation, Boston; President and Fellows of Harvard College, Cambridge, both of Mass.

[21] Appl. No.: 112,757

[22] Filed: Aug. 25, 1993

[51] Int. Cl.$^6$ ..................................................... G01N 33/53
[52] U.S. Cl. .......................... 435/7.2; 435/7.21; 435/7.23; 435/7.32; 435/287.1; 436/526; 436/806; 436/808; 324/200; 324/228; 324/244
[58] Field of Search ..................................... 436/526, 806, 436/808; 435/7.2, 7.21, 7.23, 7.32, 149, 282, 291; 324/200, 228, 244

[56] References Cited

PUBLICATIONS

Ingber et al., "Integrins as mechanochemical transducers", *Current Opinion in Cell Biology*, vol. 3, (1991), pp. 841–848.
Wang et al., "Mechanotransduction Across the Cell Surface and Through the Cytoskeleton", *Science*, vol. 260, (1993), pp. 1124–1127.
Inber et al., "The Riddle of Morphogenesis: A Question of Solution Chemistry or Molecular Cell Engineering?", *Cell*, vol. 75, (1993), pp.1249–1252.
Wang et al., "Control of Cytoskeletal Mechanics by Extracellular Matrix, Cell Shape, and Mechanical Tension", *Biophysical Journal*, vol. 66, (1994) pp. 1–9.
Albelda, S. M., et al., "Integrins and Other Cell Adhesion Molecules", *FASEB J.*, 4:2868–2880 (1990).
Bizal, C. L., et al., "Viscoelastic and Motile Properties of Hamster Lung and Peritoneal Macrophages", *J. Leukocyte Biol.*, 50:240 (1991).
Burridge, K., et al., "Focal Adhesions: Transmembrane Junctions Between The Extracellular Matrix and the Cytoskeleton", *Ann. Rev. Cell Biol.*, 4:487–525 (1988).
Cipriano, L. F., "An Overlooked Gravity Sensing Mechanism"<*The Physiologist*, 34:72 (1991).
De Groot, R. P., "Microgravity Decreases c–fos Induction and Serum Response Element Activity", *J. Cell Sci.*, 97:33 (1990).
Dennerll, T. J., et al., "Tension and Compression in the Cytoskeleton of PC–12 Neurites II: Quantitative Measurements", *J. Cell Biol.* 107:665–674 (1988).
Franke, R. P., et al., "Induction of Human Vascular Endothelial Stress Fibres by Fluid Shear Stress", *Nature*, 307:648–649 (1984).
Harris, R. C., et al., "Continuous Stretch–Relaxation in Culture Alters Rat Mesangial Cell Morphology, Growth Characteristcs, and Metabolic Activity", *Lab. Invest.*, 66(5):548554 (1992).
Hay, M., et al., "Chromatic Motin in Neuronal Interphase Nuclei: Changes Induced by Disruption of Intermediate Filaments", *Cell Motil. Cytoskel.*, 18:63 (1991).
Ingber, D. E., "Fibronectin Controls Capillary Endothelial Cell Growth by Modulating Cell Shape", *Proc. Natl. Acad. Sci. U.S.A.*, 87:3579–3585 (1990).
Ingber, D. F., et al., "How Does Extracellular Matrix Control Capillary Morphogenesis?" *Cell*, 58:803–805 (1989).

(List continued on next page.)

Primary Examiner—Toni R. Scheiner
Assistant Examiner—Susan C. Wolski
Attorney, Agent, or Firm—Arnall Golden & Gregory

[57] ABSTRACT

Mechanical stresses and deformations are applied directly to cell surface receptors or molecules and measured using a system including a magnetic twisting device in combination with ferromagnetic microbeads coated with ligands for integrins or any other surface receptors. The system can be used diagnostically to characterize cells and molecules and to determine the effect of transformation and compounds, including drugs, on the cells and molecules. The system can also be used to induce cells to grow or alter production of molecules by the cells.

21 Claims, 6 Drawing Sheets

PUBLICATIONS

Ingber, D. E., et al., "Mechanochemical Switching Between Growth and Differentiation During Fibroblast Growth Factor–Stimulated Angiogenesis In Vitro: Role of Extracellular Matrix", *J. Cell Biol.*, 109:317–330 (1989).

Janmey, P. A., et al., "Viscoelastic Properties of Vimentin Compared with Other Filamentous Biopolymer Networks", *J. Cell Biol.*, 113:155–160 (1991).

Kacahr, B., et al., "Structural Basis for Mechanical Transduction in the Frog Vestibular Sensory Apparatus: I. The Otolithic Membrane", *Hearing Res.*, 45:179 (1990).

Kolega, J., "Effects of Mechanical Tension on Protrusive Activity and Microfilament and Intermediate Filament Organization in an Epidermal Epithelium Moving in Culture", *J. Cell Biol.*, 102:1400–1411 (1986).

Komuro, I., et al., "Mechanical Loading Stimulates Cell Hypertrophy and Specific Gene Expression in Cultured Rat Cardiac Myocytes", *J. Biol. Chem.*, 266:1265–1268 (1991).

Lansman, J. B., "Single Stretch–activated Ion Channels in Vascular Endothelial Cells as Mechanotransducers?", *Nature*, 325:811–813 (1987).

Moller, W., et al., "Improved Spinning Top Aerosol–generator for the Production of High Concentrated Ferrimagnetic Aerosols", *J. Aerosol Sci.*, 21:S657 (1990).

Murti, K. G., et al., "Protein Kinase C Associates with Intermediate Filaments and Stress Fibers", *Exp. Cell Res.*, 202:36–44 (1992).

Olesen, S.–P., et al., "Haemodynamic Shear Stress Activates a $K^+$ Current in Vascular Endothelial Cells", *Nature*, 331:168–170 (1988).

Ryan, T. J., "Biochemical Consequences of Mechanical Forces Generated by Distention and Distortion", *J. Am. Acad. Derm.*, 21:115 (1989).

Sachs, F., "Ion Channels as Mechanical Transducers", *Cell Shape: Determinants, Regulation, and Regulatory Role*, 63–92 (9189).

Samuel, J.–L., et al., "Mechanically Induced Orientation of Adult Rat Cardiac Myocytes In Vitro", *In Vitro Cell Dev. Biol.*, 26:905 (1990).

Schwartz, M. A., et al., "Insoluble Fibronectin Activates the Na/H Antiporter by Clustering and Immobilizing Integrin $\alpha_5\beta_1$, Independent of Cell Shape", *Proc. Natl. Acad. Sci, U.S.A.*, 88:7849–7853 (1991).

Sims, J. R., et al., "Altering the Cellular Mechanical Force Balance Results in Integrated Changes in Cell, Cytoskeletal and Nuclear Shape", *J. Cell Sci.*, 103:1215–1222 (1992).

Sumpio, B. E., et al., "Enhanced Collagen Production by Smooth Muscel Cells During Repetitive Mechanical Stretching", *Arch. Surg.* 123:1233 (1988).

Terracio, L., et al., "Effects of Cyclic mechanical Stimulation of the Cellular Components of the Heart: In Vitro", In Vitro Cell Dev. Biol., 24:53 (1988).

Valberg, P. A., et al., "Magnetic Particle Motions Within Living Cells— Physical Theory and Techniques", *Biophys. J.*, 52:537–550 (1987).

Valberg, P. A., "Magnetometry of Ingested Particles in Pulmonary Macrophages", *Science*, 224:513–516 (1984).

Valberg, P. A., et al., "Cytoplasmic Motions, Rheology, and Structure Probed by a Novel Magnetic Particle Method", *J. Cell Biol*, 101:130–140 (1985).

Wagner, V. T., et al., "Role of a Vitronectin–like Molecule in Embryo Adhesion of the Brown Alga Fucus", *Proc. Natl. Acad. Sci. U.S.A.*, 89:3644–3648 (1992).

Watson, P. A., "Direct Stimulation of Adenylate Cyclase by Mechanical Forces in S49 Mouse Lymphoma Cells During Hyposmotic Swelling", *J. Biol. Chem.*, 265:6569–6575 (1990).

Wayne, R., et al., "The Contribution of the Extracellular Matrix to Gravisensing in Characean Cells", *J. Cell Sci.*, 101:611 (1992).

Wilson, L. J., et al., "Functional Morphology of the Telson–Uropod Stretch Receptor in the Sand Crab *Emerita Analoga*", *J. Comp. Neurol.*, 296:343–358 (1990).

Wirtz, H. R. W., et al., "Calcium Mobilization and Exocytosis After One Mechanical Stretch of Lung Epithelial Cells", *Science*, 250:1266–1269 (1990).

METHOD AND SYSTEM FOR MEASUREMENT OF MECHANICAL PROPERTIES OF MOLECULES AND CELLS

BACKGROUND OF THE INVENTION

The United States government has rights in this invention by virtue of NASA grant No. NAG-9-430 and NIH grant Nos. CA4554B to Donald Ingber, NIH grant No. HL33009 to Jeffrey J. Fredberg and NIH grant No. HL36427 to James P. Butler.

The process of recognizing and responding to mechanical stimuli is critical for growth and function of living cells. Many sensory functions including touch, hearing, baroreception, proprioception, and gravity sensation involve specialized mechanotransduction mechanisms. Development of tissue pattern is also exquisitely sensitive to changes in mechanical stress. Nevertheless, the molecular mechanism by which individual cells recognize and respond to external forces is not well understood. Stretch-sensitive ion channels, adenylate cyclase, and protein kinase C change their activity in response to applied stress, as reported by F. Sachs, in *Cell Shape: Determinants, Regulations, and Regulatory Role*, W. D. Stein and F. Bronner, eds. (Academic Press, San Diego, 1989), pp. 63–92; I. Komuro et al., *J. Biol. Chem.* 266, 1265 (1991); R. P. De Groot et al., *J. Cell Sci.* 97, 33 (1990); S. P. Olesen, et al., *Nature* 331, 168 (1988); J. B. Lansman, *Nature* 325, 811 (1987); P. Watson, *J. Biol. Chem.* 265, 6569 (1990); and T. J. Ryan, *J. Am. Acad. Derm.* 21, 115 (1989). However, these signaling pathways are likely to lie downstream from the initial mechanoreception event at the cell surface. For example, activation of these signaling molecules appears to be mediated through changes in the cytoskeleton (CSK), as reported by Komuro et al.; T. J. Ryan, *J. Am. Acad. Derm.* 21, 115 (1989); K. G. Murti, et al., *Exp. Cell Res.* 202, 36 (1992). While changes in CSK organization are an ubiquitous response to mechanical perturbation, B. Kacahr, et al., *Hearing Res.* 45, 179 (1990); L. J. Wilson and D. H. Paul, *J. Comp. Neurol.* 296, 343 (1990); L. F. Cipriano, *The Physiologist* 34, 72 (1991); T. J. Dennerll, et al., *J. Cell Biol.* 107, 665 (1988); J. Kolega, *J. Cell Biol.* 102, 1400 (1986); R. P. Franke et al., *Nature* 307, 648 (1984), the mechanism by which forces are transmitted across the cell surface and transduced into a CSK response remains unknown.

Previous analysis of mechanotransduction used standard methods to apply mechanical strain (stretch) or compressive loads and associated generalized deformation to whole cells and tissues in specialized force-sensing cells. These studies, in both plants and animals, suggest that the cell's extracellular matrix (ECM) attachments are the sites at which forces are transmitted to cells, see, for example, Kacahr, et al., (1990); Wilson and Paul, (1990); Wagner, et al., *Proc. Natl. Acad. Sci. U.S.A.* 89, 3644 (1992); R. Wayne, et al., *J. Cell Sci.* 101, 611 (1992); D. E. Ingber, *Curr. Opin. Cell Biol.* 3, 841 (1991). As in any architectural structure, mechanical loads are transmitted across the cell surface and into the cell by means of structural elements that are physically interconnected. Transmembrane ECM receptors, such as members of the integrin family, are excellent candidates for mechanoreceptors because they bind actin-associated proteins within focal adhesions and thereby physically link ECM with CSK microfilaments, as reviewed by S. M. Albelda and C. A. Buck, *FASEB J.* 4, 2868 (1990); K. Burridge, et al., *Ann. Rev. Cell Biol.* 4, 487 (1988). The possibility that ECM receptors mediate mechanotransduction is supported by the finding that stretching flexible ECM culture substrata alters CSK organization and induces biochemical changes in adherent cells, reported by Wirtz and Dobbs, *Science* 250, 1266 (1990); Samuel and Vandenburgh, *In Vitro Cell Dev. Biol.* 26, 905 (1990); Harris, et al., *Lab. Invest.* 66, 548 (1992); Sumpio, et al., *Arch. Surg.* 123, 1233 (1988); Terracio, et al., *In Vitro Cell Dev. Biol.* 24, 53 (1988).

However, in these and other stretching studies, it is not possible to separate effects due to transmembrane force transfer from those due to global shape changes and generalized deformation of the plasma membrane and CSK.

It is therefore an object of the present invention to provide a method and system for applying controlled mechanical loads directly to specific molecules, either isolated or expressed on cell surfaces, for characterizing molecules and cells and their properties.

It is a further object of the present invention to provide a method and system for applying controlled mechanical loads directly to specific molecules to test compounds potentially affecting molecules and cells to determine if the compounds affect the mechanical properties of the molecules and cells, and the extent of this affect.

It is another object of the present invention to provide a method and system which can separate effects due to specific transmembrane force transfer from those due to global shape changes and generalized deformation of the plasma membrane and cytoskeleton.

It is another object of the present invention to provide a method and system which can assess the status of the cell with respect to the mechanical properties, strength, shape, stiffness, rheology, proliferation, and other factors relevant to the health and function of the cell.

SUMMARY OF THE INVENTION

Mechanical stresses are applied directly to specific molecules, either within or as expressed on cell surfaces or on non-cellular substrates, using a system including a magnetic twisting device in combination with ferromagnetic microbeads coated with attachment molecules. Examples of molecule-specific attachment molecules include ligands for integrins (e.g., extracellular matrix molecules, synthetic ECM peptides, and anti-integrin antibodies), and other molecules binding to non-integrin surface-bound molecular receptors (for example, ligands for cell-cell adhesion receptors "cadherins", that also link up to the cytoskeleton). "Non-specific" ligands can also be used as attachment molecules. Cells can be living or dead, intact or permeabilized. The cells or isolated molecules are immobilized so that their interaction with the ferromagnetic beads can be manipulated by application of magnetic forces.

The system is used (1) to apply stresses to cells without inducing global shape change, (2) to measure those stresses, (3) to measure resulting (local) distortions, and (4) to measure changes in these quantities using a wide variety of biological interventions, protocols and circumstances. In the simplest case, one can measure the avidity of protein-protein binding by quantitating the ability of the bound complex to resist mechanical perturbation (twisting). This approach can be used to screen for high affinity ligands or to quantitate the mechanical properties (stiffness or elasticity, permanent deformation, viscosity or rheology) of synthetic or naturally produced materials, fabrics, filters, etc. In a more complex case, one can measure the mechanical properties of intact living cells, by twisting specific molecules that are exposed on the cell surface and are physically interconnected with the molecular scaffoldings, or cytoskeleton, that form the structural backbone of the cell.

The system can be used diagnostically to characterize cells and to determine the effect of transformation and compounds, including drugs, on the cells, thereby forming the basis of a screen for useful modulators of cell shape, growth and function. The system can also be used to induce gene expression, alter production of molecules by the cells, or mechanically disrupt membrane continuity and thereby permit transmembrane delivery of large molecules.

BRIEF DESCRIPTION OF THE DRAWINGS

FIG. 4a, angular strain (degree) versus stress (dyne/cm$^2$); FIG. 4b, stiffness (dyne/cm$^2$) versus stress (dyne/cm$^2$).

DETAILED DESCRIPTION OF THE INVENTION

The System

To determine whether any particular receptor system, such as ECM receptors, provide a specific molecular path for mechanical signal transfer to the cytoskeleton (CSK), a method was devised in which controlled mechanical loads can be applied directly to specific cell surface molecules without producing global changes of cell shape. The method is shown schematically in FIG. 1. In this device, these loads can not only be applied, but also the load and the resulting deformation measured.

Figure 1:
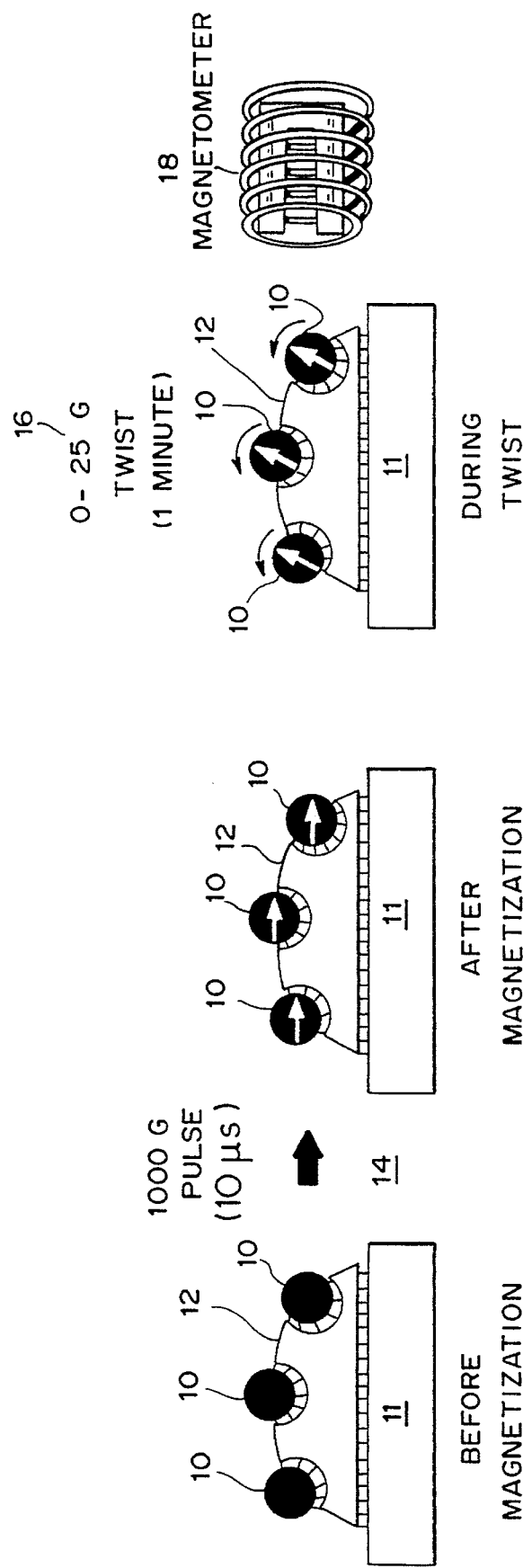
FIG. 1 is a schematic of the method using the magnetic twisting device.

As shown by FIG. 1, in one embodiment, ferromagnetic microbeads 10 coated with molecular ligands are allowed to bind to their corresponding molecular receptors on the surfaces of cells 12 for 10 to 15 minutes and unbound beads are removed before magnetic manipulation is initiated. Cells 12 are adhered to plastic dishes 11, or otherwise immobilized, for example, within a gel matrix. In a second embodiment (not shown), molecules are adhered to or immobilized on a surface or within a volume other than a cell and bound by the attachment molecules on the ferromagnetic beads. Brief application of a strong external magnetic field 14 (1000 Gauss for 10 µs) results in magnetization and alignment of the magnetic moments of all surface-bound beads 10. Defined mechanical stresses (0–100 dynes/cm$^2$, preferably 0–68 dynes/cm$^2$) are then applied without remagnetizing the beads using a weaker "twisting" magnetic field 16 (0–100 Gauss, preferably 0–25 Gauss) applied perpendicular to the original field. The average bead rotation (angular strain) induced by the twisting field is quantitated using a magnetometer 18 to measure changes in the component of the remanent magnetic field vector in the direction of the original magnetization as a function of time. In the absence of force transmission across the cell surface, the spherical beads would twist in place by 90° into complete alignment with the twisting field, and the remanent field vector would immediately drop to zero. In contrast, transmission of force to the CSK would result in increased resistance to deformation and decreased bead rotation.

This cell magnetometry system was originally described by Bizal, et al., *J. Leukocyto Biol.* 50, 240 (1991); Valberg and Butler, *Biophys. J.* 52, 537 (1987); Valberg and Albertini, *J. Cell Biol.* 101, 130 (1985); and Valberg, *Science* 2224, 513 (1984), for use in measuring viscoelasticity in living cells that contained ingested or injected ferromagnetic particles.

As described herein, this system is modified such that ferromagnetic microbeads are coated with specific receptor ligands, for example, which mediate attachment or spreading, which are bound to molecules on the external surface of or specific molecules within the cells to be characterized. By magnetizing these surface-bound beads in one direction and then applying a second weaker magnetic field oriented at 90°, it is possible to twist the beads in place and thereby exert a controlled shear stress (0–100 dynes/cm$^2$, preferably 0–68 dynes/cm$^2$) on bound cell surface receptors. An in-line magnetometer is used to simultaneously measure changes in the orientation of the magnetized beads and hence, quantitate angular strain produced in response to the applied stress.

This system can be altered by varying the amplitude of the twisting magnetic fields using any desired time history, such as a square wave or sine wave function. The device can also be modified to allow systematic probing with magnetic torques applied both in-plane and out-of-plane with respect to the plasma membrane. To the extent that the CSK of the cell allows long range force transmission, the out-of-plane torques may exert effects further into the cell interior. Sinusoidal probing and varying the frequency of force application also permit quantitation of CSK stiffness and hysteresis as well as dynamic stress-induced CSK remodeling or plastic deformation, allowing more precise definition of specific cytomechanical signatures that characterize changes in cell function, by analyzing differences in cell mechanics induced by different forms of force application (sine wave, square wave, triangular wave, etc.), and different frequencies of force application.

Microbeads

Ferromagnetic microbeads are selected for use since, unlike paramagnetic beads, they remain magnetized after removal of a magnetic field. Paramagnetic beads are not useful in the method described herein.

Beads are selected which preferably have a particle size between 0.1 to 500 micron for use with animal or plant cells. Microbeads for use in characterizing bacteria and compounds affecting bacteria are preferably smaller, in the range of 0.03 to 0.1 micron. Beads having a diameter of between 0.1 and ten microns are preferred, although the larger beads could work well with larger cells such as oocytes. Suitable beads having an iron oxide ($Fe_2O_3$ or $Fe_3O_4$) core can be obtained from Drs. Moller and Stahlhofen of Germany.

Attachment of Molecular Receptor Ligands to Microbeads

The microbeads are coated with molecular receptor ligands, or "attachment molecules", which bind to surface molecules on the cells to secure the microbeads to the cell cytoskeleton, or to molecules which are immobilized either on cell or synthetic substrates. The attachment molecules can be molecule-specific ligands such as antibodies to extracellular matrix molecules, specific ligands for integrins or specific ligands for other non-integrin receptor systems, as defined in more detail below. The attachment molecules can also be non-specific ligands such as lectins which bind to surface molecules. These are collectively referred to herein as "attachment molecules", unless otherwise specified.

The attachment molecules can be secured to the microbeads by absorption, chemical conjugation, or other methods known to those skilled in the art. In the preferred embodiment, the attachment molecules are bound to the microbeads in a concentration of at least 1 ng/cm$^2$ of bead surface, for example, using a protein coating solution concentration of 50 µg/ml or higher added in a carbonate buffer to beads at 1 mg/ml (which represents a significant excess of the required amount to achieve the desired concentration), stored for over three hours at 4° C.

There are numerous attachment molecules, both naturally occurring and synthetic. Examples of naturally occurring attachment molecules are matrix molecules that associate with integrins or with other receptors that span the cell surface and physically interconnect with distinct cytoskeletal proteins. Examples of cytoskeletal proteins are talin, vinculin, α-actinin, paxillin, zyxin, and actin. Examples of naturally occurring attachment molecules include fibronectin, vitronectin, collagens, laminin, fibrinogen, fibulin, dystrophin, heparan sulfate proteoglycan, plasminogen activator/urokinase, gangliosides, Von Willebrand's factor, entactin, venoms such as Echistatin, lectins, and antibodies. Synthetic molecules include synthetic RGD containing peptides, such as the Arg-Gly-Asp (RGD) amino acid sequence that is a known ligand for fibronectin receptors. Molecules made synthetically can be made by chemical attachment of amino acids or expression of synthetic nucleic acid sequences in appropriate host systems. Other types of transmembrane molecules that interconnect with CSK filaments and which transfer external mechanical signals to the CSK such as cadherins, as well as cell surface proteoglycans such as heparan sulfate proteoglycans, can also be used.

Molecules and Cells That Can Be Tested

Molecules

The system can be used with molecules immobilized onto a surface, alone or as a complex, in the same manner as the system is used with molecules attached to cell surfaces. The same technology is used to bind the molecules to be tested as to bind the attachment molecules to the microbeads. For example, ligands such as antibodies or avidin can be bound to the microbeads and receptors such as antigens or biotin immobilized in microwell plates, then the mechanics of the molecular interactin measured.

Cells

Any type of cell, living or dead, with surface receptors, can be used in this system. This includes mammalian cells and other types of animal cells, plant cells, yeast cells, and bacterial cells. Examples of animal cells include not only cells making up tissue and circulating cells, but also larger specialized cells such as oocytes. In a preferred embodiment, the cells are alive, although frozen tissue samples can be readily assayed. It should be possible to measure the properties of dead cells as well, although not if the cells have been fixed (artificially rigidified). For example, frozen slices for histology would be coated and fixed in place on slides (using subbed slides, for example), then analyzed. Cells may be obtained from cell culture or dissociated from tissue using standard techniques such as exposure to collagenase.

Studies have been conducted on a wide variety of adherent cells, including endothelial cells, hepatocytes, arterial smooth muscle cells, myogenic cells, breast cancer cells; and floating cells including cancer cell lines.

Cells can be physically or chemically coupled to a substrate in order to be evaluated using the system, or immobilized, for example, in an agarose gel. Cells do not have to be adherent to a surface per se, however, they do have to be held in place so that magnetic twisting does not simply result in rotation of the entire cell. In the case of adherent cells, the cells independently bind to a surface. In the case of floating cells, the cells are mixed first with beads, the unbound beads and cells are separated using conventional separation methods, and the remaining cells having beads bound thereto are mixed with melted agarose gel. The gel hardens at temperatures less than 50° C. and the cells are ready for testing in the system.

System Variables

The system specifically allows measurement of cytoskeletal strain, stiffness, elastic recoil, and viscoelasticity in response to any cell manipulation or microenvironmental alteration. The same system can be used to analyze the mechanical load-bearing function of any cell surface receptor, by changing the specific ligand attached to the microbeads.

The sensitivity of a cell to a mechanical stimulus may be altered by changing the environment of the cell at its surface or in its interior. The surface environ includes but is not limited to: attachment molecules, their concentration, location, and adhesion strength, and the presence or absence of inhibitors and activators. The interior environment includes those CSK elements mechanically linked to the surface receptors. These can be altered by the number of ECM contacts, the shape of the cells, the energy state of the cell (presence of ATP), membrane continuity, the size of the bead, the growth state, and contractile state.

For diagnostic purposes, control cells are compared with cells to be characterized. Cells are classed by examples of different types of cells to be tested including cells that have been characterized in terms of their sensitivity to specific drugs or their state of malignancy or invasive or metastatic capabilities.

Binding of Beads to Cells

In most cases, beads are added to cells that are already adherent and allowed to bind for approximately ten to thirty minutes, although this can range from two minutes up to hours, in a ratio that typically ranges from two beads:cell to fifty beads:cell. In the case of floating cells, the cells are mixed first with beads at a ratio of between one cell:two beads to one cell:twenty beads, the unbound beads and cells are separated, and the remaining cells having beads bound thereto are immobilized in an agarose gel.

Method for Characterizing Molecules and Cells

The magnetic moments of the surface-bound beads are aligned by application of a brief but strong external magnetic field, 250 gauss or greater, as compared to the coersive field within the microbeads, which is generally in the range of 50 to 150 gauss. Duration of the magnetic field ranges from microseconds to seconds, until the beads are magnetized. This is typically in the range of 1000 Gauss for one to ten microseconds. Defined mechanical torque is then applied to the beads using a weaker "twisting" magnetic field of zero to 100 Gauss, preferably zero to 25 Gauss applied perpendicular to the original field. Bead rotation (angular strain) produced by the twisting field is quantitated using the magnetometer to measure changes in the component of the remanent magnetic field vector in the direction of the original magnetization, that is, changes in the direction of the field that is associated with the beads themselves.

In the absence of force transmission across the cell surface, there is little resistance to bead rotation. In this case, the spherical beads twist by 90°, coming into complete alignment with the twisting field and the remanent field vector in the direction of the original magnetization drops to zero. In contrast, successful transmission of force to the cytoskeleton results in increased resistance to deformation and hence, decreased bead rotation.

This method is distinct from those previously used since it involves binding to specific molecules that are on cell surfaces and which may interlink with cytoskeleton. In contrast, prior existing methods (e.g., cell poking, micropipette aspiration) apply force to "cell surfaces" non-specifically, and the effectiveness of the resulting force transfer to the CSK depends to a large degree on the extent to which the cell membrane is deformed. The system described herein allows application of a defined local rotational shear stress to specific surface receptors and measurement of a force-induced cytoskeletal response, without producing a global shape change. In contrast to the other methods, the magnetically manipulated beads are bound to receptors expressed on the surface of the cells or specific intracellular molecules or structures within the cells. As used herein these are referred to collectively as "molecules immobilized on the surface of cells which are bound by attachment molecules on the microbeads", unless otherwise stated.

Screening of Compounds Affecting Cells

As noted above, both immobilized molecules and molecules expressed on or bound to cell surfaces can be manipulated using the system described herein. An advantage of the method is that living cells can be assayed since the method does not injure living cells. Stimulation is used to alter cell state, i.e., resting versus proliferation, or to stimulate production of certain molecules associated with a particular state. Stimulation of growth signaling pathways is an excellent model to screen for growth inhibitors. The same holds true for any other function, e.g., differentiation, secretion, motility, mitosis, etc. Any cell, organism, or material, for that matter, can be tested and its mechanical properties measured, as long as it exhibits accessible and specific molecular determinants. In the case of yeast or bacteria, one can use antibodies against specific cell wall components, peptidoglycans, etc., for example, as a rapid assay for identifying new antibiotic analogues that work by disrupting cell wall continuity.

One would select certain cell types for characterization of particular molecules or the effects of certain compounds on these molecules and/or cells. For example, capillary cells can be used to screen for angiogenesis modulators, smooth muscle cells for drugs that alter their contractility and may be useful for hypertension, osteoclasts for osteoporosis drugs, tumor cells for drugs for invasion and metastasis, parasites for anti-parasitic drugs, bacteria, fungi, and other microorganisms for anti-microbials, plant spheroplasts for chemicals that modulate plant growth and development, and virusus for anti-virals.

This system is particularly useful in detection of a response induced by exposure of the cells to a compound, and is therefore of value in screening for compounds which produce an effect on the cells, in particular in cell form, growth and function. For therapeutics, cells are held in place using adsorption, receptor ligation, chemical conjugation, or embedding, and then magnetic twisting is initiated. In distinction from the previous methods utilizing mechanical manipulation, this system allows one to apply defined mechanical loads to specific cell surface receptors without altering global cell shape. Accordingly, one can screen for compounds altering cell shape, cell stiffness, strength, and interference with the action of specific integrins or other cytoskeletal components interactive with surface receptors. The system can define specific cytomechanical parameters such as stiffness, elastic recoil, and apparent viscosity, that are characteristic for specific cells or cell shapes. Specific cell shapes can be used to predict whether cells will grow, migrate, or differentiate. It is therefore possible to screen for potential pharmaceutical agents which modulate growth or differentiation based on their ability to produce a characteristic cytomechanical change.

This approach is particular useful in toxicology laboratories for screening potentially toxic compounds, mutagens, and teratogens, as well as compounds which produce a beneficial effects, such as chemotherapeutic agents. It is also potentially useful in screening for therapeutic agents that might modulate such processes as hearing, blood pressure control, barioreception, touch, gravity sensation in animals, and both gravitropism and thixotropism in plants.

Diagnosis of In Situ Changes in Cell Structure and Function

The same approach can be used in patients by injecting the magnetic microbeads into the vasculature or directly into tissues or tumors. An external magnetometry device is then used to characterize the mechanics of cell in a local area of interest, for example, by showing that tumor cell growth is characterized by a specific cytomechanical behavior, one can then look for the specific cytomechanical behavior to detect the presence of the tumor, or conversely, to measure the response to a pharmaceutical agents, such as an anti-cancer drug or angiogenesis inhibitor. The potential for metastasis of a tumor can also be determined by determining that certain tumors that are highly migratory exhibit a characteristic cytomechanical behavior, and determining that a patient tumor has the same characteristic.

The following examples demonstrate the utility of the system for characterization of screening for the effect of specific chemotherapeutic agents. These compounds, taxol and AGM-1470, are currently being used for treatment of solid tumors and produce a characteristic cytoskeletal signature that is only measurable using this system.

Example 1

Measurement of Transmembrane Force Transfer in Living Endothelial Cells

Adherent endothelial cells were first allowed to bind beads coated with a synthetic peptide containing the Arg-Gly-Asp (RGD) sequence that is a known ligand for fibronectin receptors, such as integrin $\beta_1\alpha_5$, which these cells express on their surface. Transmembrane force transfer was then measured.

Attachment molecules were bound to cells as follows: Capillary endothelial cells were plated ($3\times10^4$/well) on fibronectin-coated bacteriological plastic 96 well plates from Removawells, Immunolon Ill, and cultured for 6–10 hr in chemically-defined medium described by Ingber *Proc. Natl. Acad. Sci. U.S.A.* 87, 3579 (1990); Ingber and Folkman, *J. Cell Biol.* 109, 317 (1989); and Ingber and Folkman, *Cell* 58, 803 (1989), before bead addition. Spherical ferromagnetic beads (5.5 μm diameter, 1 mg/ml; described by Moller, et al., *J. Aerosol Sci.* 21, S657 (1990)) were coated with proteins at a concentration of 50 μg/ml, although lower concentrations may also be used. RGD-containing peptide (Peptite 2000, obtained from Telios), acetylated low density lipoprotein (AcLDL), bovine serum albumin (BSA) or anti-integrin $\beta_1$ antibodies as described by Schwartz, et al., *Proc. Natl. Acad. Sci. U.S.A.* 88, 7849 (1991).

Figure 2:
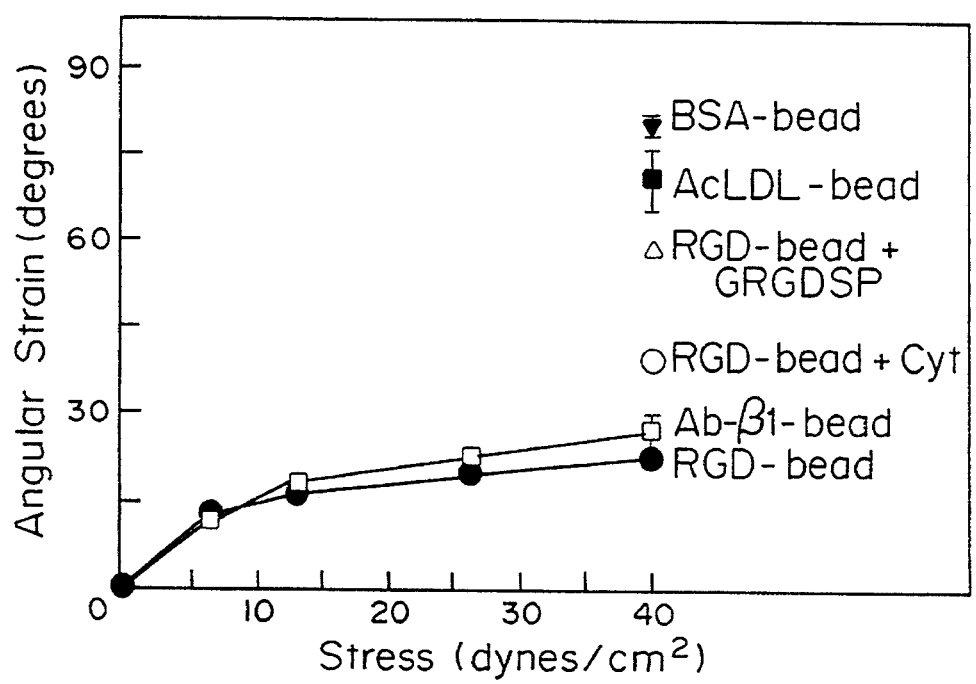
FIG. 2 is a graph of the stress-strain relation measured using magnetic microbeads attached to the surfaces of living cells. Applied stress was determined by a calibration technique in which the same beads were twisted in a standard solution of known viscosity of 1000 poise. Angular strain (bead rotation) was calculated as the arc cosine of the ratio of remanent field after 1 min twist to the field at time 0. Angular strain is plotted here as degrees. Bead coating: RGD, Arg-Gly-Asp-containing synthetic peptide; Ab-$\beta_1$; AcLDL, acetylated-low density lipoprotein; BSA, bovine serum albumin. GRGDSP, soluble fibronectin peptide (1 mg/ml added for 10 min); Cyt, cytochalisin D (0.1 µg/ml). BSA-bead: inverted triangle; AcLDL-bead, closed square; RGD-bead+GRGDSP, open triangle; RGD-bead+Cyt, open circle; Ab-$\beta$1-bead, open square; RGD-bead, closed circle. Error bars, SEM.

The results are shown in FIG. 2. Efficient transmembrane force transfer was observed in cells bound to RGD-beads; the cells became stiffer and increased their resistance to mechanical deformation (bead twisting) at higher levels of applied stress, such that angular strain only reached a bead rotation of approximately 25°.

To demonstrate the specificity of transmembrane force transfer, soluble synthetic peptide, Gly-Arg-Gly-Asp-Ser-Pro (1 mg/ml), was included in the culture medium as a competitor. As also shown by FIG. 2, this fibronectin peptide inhibited CSK stiffening whereas a control hexapeptide with a single amino acid substitution (Gly-Arg-Gly-Glu-Ser-Pro) had no inhibitory effect.

Beads coated with antibodies directed against integrin $\beta_1$ receptor subunits (obtained from Biosource and attached as described above at 50 μg/ml or higher in a carbonate buffer with beads added to 1 mg/ml and stored at 4° C. for over three hours) produced a similar stiffening response. In contrast, surface-bound beads coated with non-specific cell attachment ligands, such as acetylated-low density lipoprotein (AcLDL) or bovine serum albumin, were not nearly as restricted in their rotation. AcLDL binds to specific transmembrane receptors on the endothelial cell surface, however, they do not normally play a role in cell adhesion. The small but statistically significant resistance to deformation that these beads did exhibit (deviation from 90°) may be due to generalized distortion of elements of the submembranous cytoskeleton that are known to be highly deformable. Local non-specific CSK deformation was also observed when this cell magnetometry system was used in the past with ingested ferromagnetic particles that were uncoated, irregularly shaped, and contained within intracellular lysosomes. Thus, establishment of a specific molecular path for force transmission appears to be required for efficient signal transfer as well as an effective CSK response.

To confirm that applied mechanical loads were indeed transmitted to the CSK, the mechanical properties of cells bound to RGD-beads were measured before and after disrupting microfilament lattice integrity with a low concentration of cytochalasin D (0.1 μg/ml) that had minimal effects on cell shape.

The results are shown in FIG. 2. Angular strain increased after only 15 minutes exposure to cytochalasin. Efficient force transfer and associated CSK stiffening also correlated with focal adhesion formation, as defined by recruitment of talin, vinculin, and α-actinin to the site of bead binding. These focal adhesion proteins, which appeared along the surface of RGD-beads but not AcLDL-beads, form the molecular bridge that physically interlinks integrins with actin microfilaments. Recruitment of talin also appears to be required for cell spreading on ECM.

Figure 3:
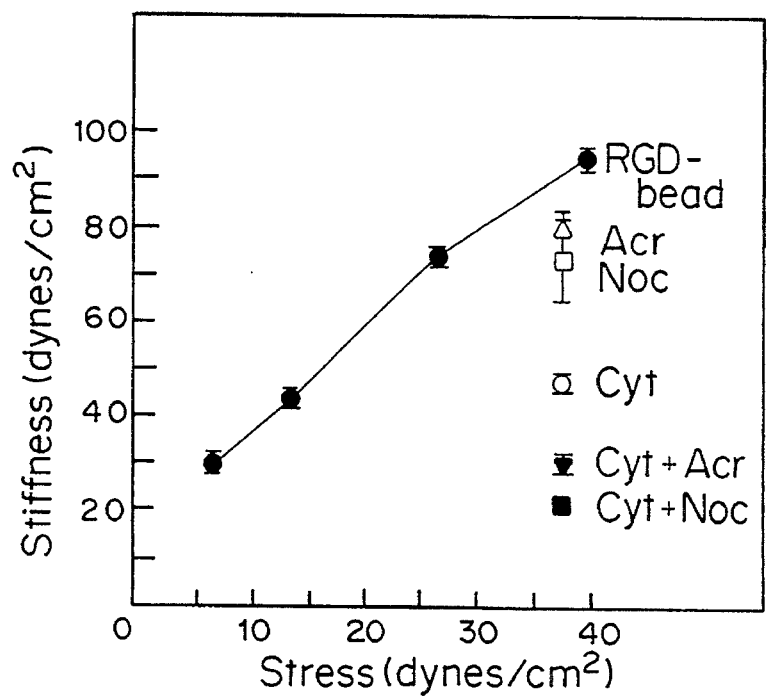
FIG. 3 is a graph of the stiffness (dynes/cm$^2$) of the CSK of living cells, defined as the ratio of stress to strain (in radians) at 1 min twisting. Noc, nocodazole (10 µg/ml); Acr, acrylamide (4 mM); Cyt, cytochalasin D (0.1 µg/ml). RGD-bead, closed circle; Acr, open triangle; Noc, open square; Cyt, open circle; Cyt+Acr, inverted triangle; Cyt+Noc, dark square.

Importantly, disruption of microfilament lattice integrity using cytochalasin D did not completely suppress CSK stiffening, as shown by FIG. 3, suggesting that other filament systems may also contribute to the CSK response to force. Disruption of microtubules or intermediate filaments using nocodazole (10 μg/ml) or acrylamide (4 mM; Hay and De Boni, *Cell Motil. Cytoskel.* 18, 63 (1991)), respectively, inhibited the stiffening response by approximately 25% and no additive effect was observed when they were combined. Combining cytochalasin D with acrylamide reduced stress-induced CSK stiffening by more than 85% and with nocodazole resulted in complete suppression. Thus, while integrins may initially transmit forces to microfilaments within focal adhesions, higher order structural interactions between all three CSK filament systems appear to be responsible for efficient transduction of the mechanical stimulus into a cellular response. The finding that actin microfilaments contribute the most to cell stiffness is consistent with recent data by Janmey, et al., *J. Cell Biol.* 113, 155 (1991), which show that networks of purified actin polymers exhibit a higher shear modulus than networks containing microtubules or intermediate filaments.

These results demonstrate that the system and methods described herein can be used to induce focal adhesion formation, which supports a force-dependent stiffening response while beads coated with non-adhesion receptors do not. Cytoskeletal stiffness (ratio of stress to strain) increased with the applied stress and required intact microtubules and intermediate filaments as well as microfilaments. These results indicate that integrins, for example, or other receptors, can act as mechanoreceptors and transmit mechanical signals to the cytoskeleton. Mechanotransduction, in turn, can be mediated simultaneously at multiple locations inside the cell through force-induced rearrangements within a tensionally-integrated cytoskeleton.

Example 2

Comparison of Transmembrane Force Transfer in Living and Dead (Permeabilized) Endothelial Cells Under Different Experimental Conditions Methods Bovine capillary endothelial cells were cultured to confluence, serum deprived, trypsinized, and plated in defined medium on fibronectin (FN)-coated 96 wells (Removawells, Immulon II, Dynatech) as previously described (Ingber, 1990). The shape of adherent cells was varied from round to spread by increasing the FN coating density from 10 to 500 ng/cm$^2$. Projected areas of adherent cells were determined using a computer image analysis system (Ingber, 1990). A total of 45 cells within five randomly selected areas from three different culture wells was measured for each cell area determination.

After adherence to high FN for 3 hrs, some of the cells were permeabilized as described by Sims et al., *J. Cell Sci.* 103:1215–1222 (1992). In brief, cell adherent to high FN were washed once in a CSK stabilization buffer (50 mM KCl, 10 mM imidazole, 1 mM EGTA, 1 mM MgSO$_4$, 0.5 mM dithiothreitol, 5 µg/ml aprotinin, 5 µg/ml leupeptin, 0.1 mM PMSF, and 20 mM PIPES, pH 6.5) which preserves contractile microfilaments in a functional form. Cells were then incubated in the same buffer containing saponin (25 µg/ml; Sigma, St. Louis, Mo.) for 10 min at 37° C. Cells were induced to retract by incubation in a tension-generation buffer containing 250 µM ATP (250 µM CaCl$_2$, 50 mM KCl, 1 mM EGTA, 2 mM MgSO$_4$, 0.5 mM dithiothreitol, 5 µg/ml aprotinin, 5 µg/ml leupeptin, 0.1 mM PMSF, 2M glycerol, and 25 mM PIPES, pH 7.0).

CSK mechanics were quantitated using a twisting device in which controlled mechanical loads were applied directly to apical cell surface receptors without producing any global cell shape change. In brief, cells adherent to FN-coated wells for 3 to 10 hrs were allowed to bind to spherical ferromagnetic beads (5.5 µm or 1.4 µm diameter) that were precoated with a synthetic RGD-containing peptide (Telios). After 10 to 20 min., unbound beads were washed away with 1% BSA in DMEM and the wells were individually placed into the magnetic twisting device and maintained at 37° C. A brief (10 µs) but strong (1000 gauss) homogeneous magnetic pulse was then applied to magnetize all surface bound beads in the horizontal direction. After 20 sec, a twisting torque was applied by applying a weaker magnetic field (0–15 gauss) in the vertical direction for 1 min. Because this field was small, it did not realign the bead magnetic moments, rather rotated the beads in place in the same direction. The extent of bead rotation was measured by an in-line magnetometer which continuously detected the magnitude of the bead magnetic vector in the horizontal direction. The torque of the applied twisting field is proportional to the twisting field, bead magnetization, and the sine of the angle between the twisting field vector and the bead magnetization vector. The resulting shear stress was transmitted to the cell through the bead-integrin interaction, causing the cell to deform. Applied stress, angular strain, and stiffness (ratio of stress to strain) were quantitated. The twisting field was then turned off for 1 min and the extent of recovery of the bead magnetic signal after twisting, a measure of the energy stored elastically in the cell, was quantitated. Permanent deformation (percentage of angular strain that was sustained after applied stress was released) of the cell was determined from the unrecovered bead magnetic signal (remaining deformation) after removing the applied stress. Apparent viscosity was calculated as the product of stiffness and time constants of recovery after the applied stress is removed.

Results

Figure 4A:
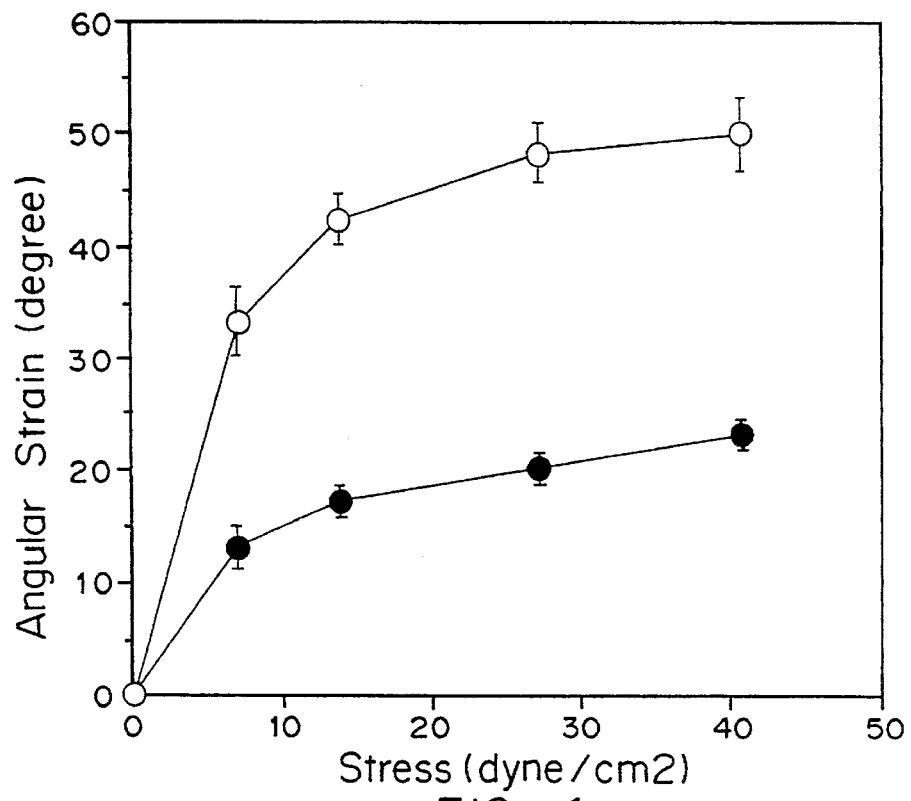
FIGS. 4a and 4b are graphs of the angular strain and stiffness of round cells (cells on low fibronectin, 10 ng/cm$^2$) (open circles) and spread cells (cells on high fibronectin, 500 ng/cm$^2$) (closed circles) as stress was applied from 7 to 40 dyne/cm$^2$.
Figure 4B:
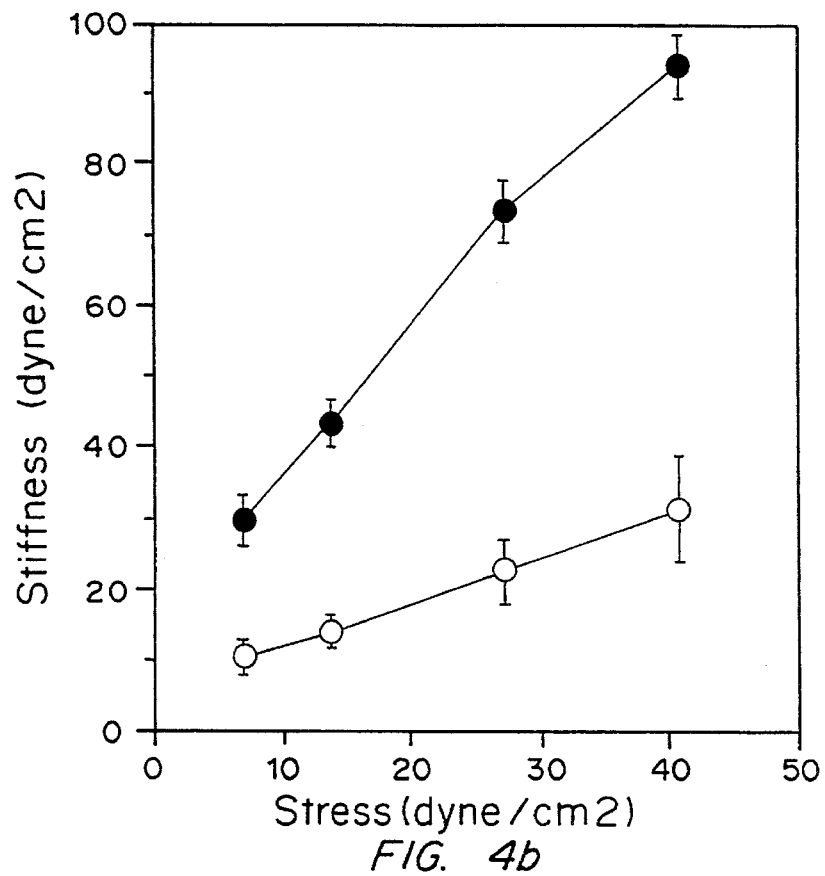
Figure 5:
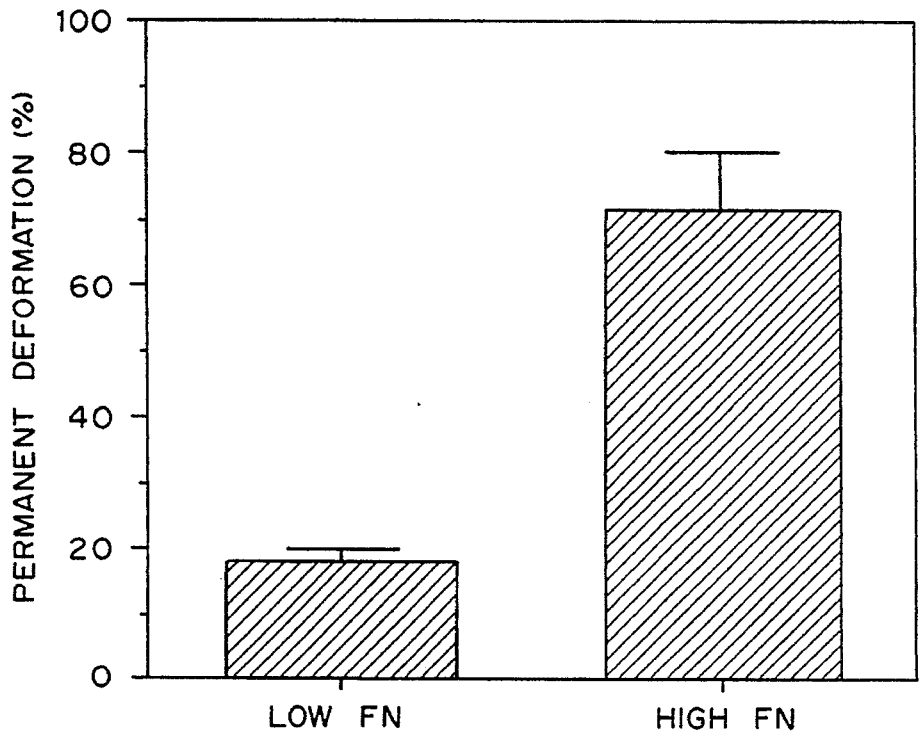
FIG. 5 is a bar graph of the permanent deformation (%) for round cells (cells on low fibronectin, 10 ng/cm$^2$) and spread cells (cells on high fibronectin, 500 ng/cm$^2$), after the applied stress (40 dyne/cm$^2$) was removed.

Studies were carried out to discriminate the effect of ECM, cell shape and mechanical tension on CSK mechanics. Increasing the FN density from low to high promoted cell spreading and resulted in a five fold increase in projected cell areas (from 350 µm$^2$ to 1640 µm$^2$) when measured after 6 hours of plating. Round and spread cells both exhibited non-linear stress-strain relationships, however, greater angular strains were observed in response to the same applied stresses in cells on low FN when compared to those on high FN, as shown by FIG. 4a. Stress-induced stiffening was also observed in cells on both FN densities, but the stiffening response (slope of stiffness vs stress) was 50% lower in the round cells than in the spread cells, as shown by FIG. 4b. The permanent deformation of the CSK and the apparent viscosity in spread cells were about three times higher in spread cells than in round cells, as shown by FIG. 5.

To confirm that magnetic beads on the cell surface were probing three dimensional structures within the CSK lattice rather than the membrane or cortical CSK alone, beads of different diameters (5.5 µm vs 1.4 µm) were used for stress application. If one were only measuring properties of cell cortex, then, at a given stress, angular strain should decrease by three fold and stiffness should increase by three fold due to the associated decrease in the area over which the same stress was applied using the 1.4 µm beads, since angular strain is directly proportional to bead diameter. However, application of stress over small RGD-coated beads resulted in similar angular strain and hence, stiffness, at low applied stresses. Furthermore, at higher levels of applied stress, the smaller bead exhibited relatively decreased stiffening. This result was the opposite of that which would be obtained if only two dimensional structures were being probed. Apparent viscosity was 50% when measured with smaller beads than measured with larger beads at higher applied stress, corresponding to the differences in stiffness at higher applied stresses; there were little differences in the permanent deformation measured with either bead.

To discriminate between dynamic and static properties of the CSK, cell membranes were permeabilized with the detergent, saponin (25 µg/ml).

Permanent deformation is determined as follows: measure the remaining strain after the applied stress is released from about 1 min or longer, take the ratio of remaining strain to angular strain—this is permanent deformation.

Apparent viscosity is determined as follows: measure the time constant of recovery after the applied stress is released, multiply the time constant with stiffness, one will get apparent viscosity.

Figure 6:
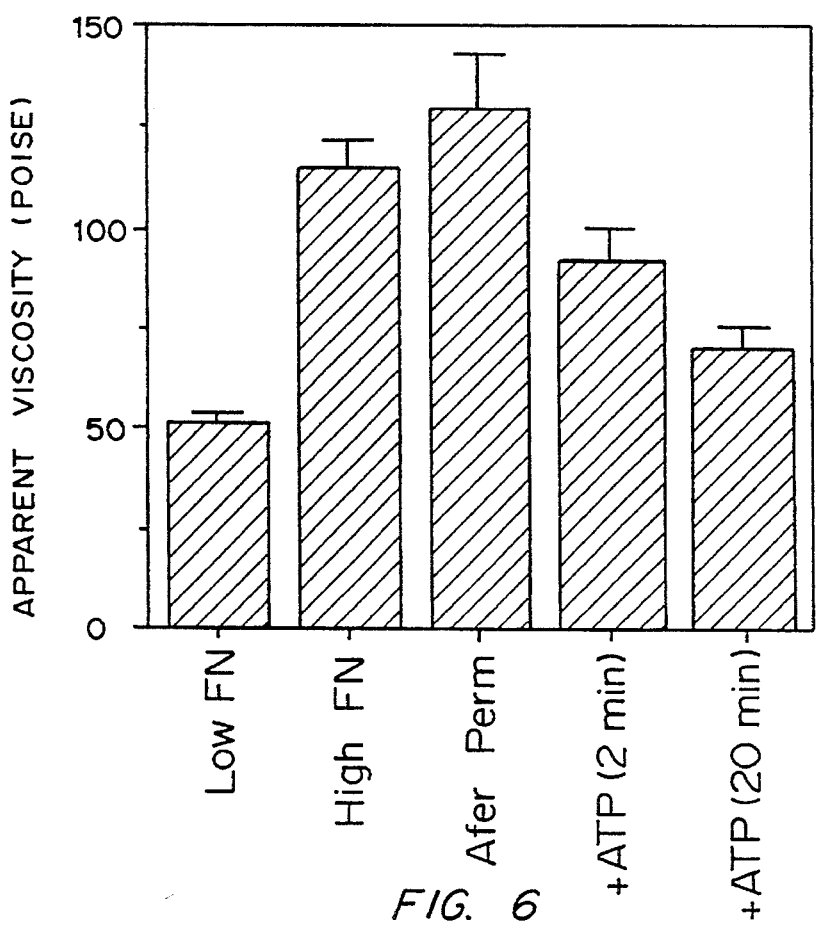
FIG. 6 is a graph of the apparent viscosity (poise) of spread cells (high fibronectin), round cells (low fibronectin), saponin membrane permeabilized spread cells without ATP (after Perm), 2 minutes after adding ATP to permeabilized cells (+ATP, 2 min), and 20 minutes after adding ATP to permeabilized cells (+ATP, 20 min).

The resulting loss of membrane continuity and depletion of cytoplasmic ATP resulted in a 20% increase in both CSK stiffness and apparent viscosity, as shown by FIG. 6, while permanent deformation decreased by more than half. Addition of ATP (250 µM) to membrane-permeabilized cells resulted in progressive decreases in CSK stiffness and apparent viscosity which were detectable within 2 minutes following ATP addition, prior to any measurable change in cell size, as also shown by FIG. 6. A significant decrease in permanent deformation was observed after 20 min of ATP addition, once the CSK lattice had physically retracted; there was no change in permanent deformation at early times. CSK stiffness also increased in proportion to applied stresses in membrane-permeabilized cells, as observed in intact cells, even though both transmembrane osmotic pressure differences and membrane continuity were lost. However, the stiffening response appeared to be compromised in membrane-permeabilized cells.

Example 3

Comparison of Normal and Tumor Cells

Since this non-invasive technique probes the very structure of the cell, it offers the possibility to identify specific cytomechanical "signatures" that are prognostic of changes in cell growth as well as neoplastic transformation. As demonstrated by Ingber (1990), alterations in CSK mechanics were measured that correlated directly with changes in cell shape, which in turn are predictive of changes in proliferation in normal, non-transformed cells. Specifically, cytoskeletal stiffness and cell growth increase in parallel as cell spreading is promoted. In contrast, tumor cells exhibited both different mechanical properties, i e , they were less "stiff", and deregulated growth under similar culture conditions.

Figure 7:
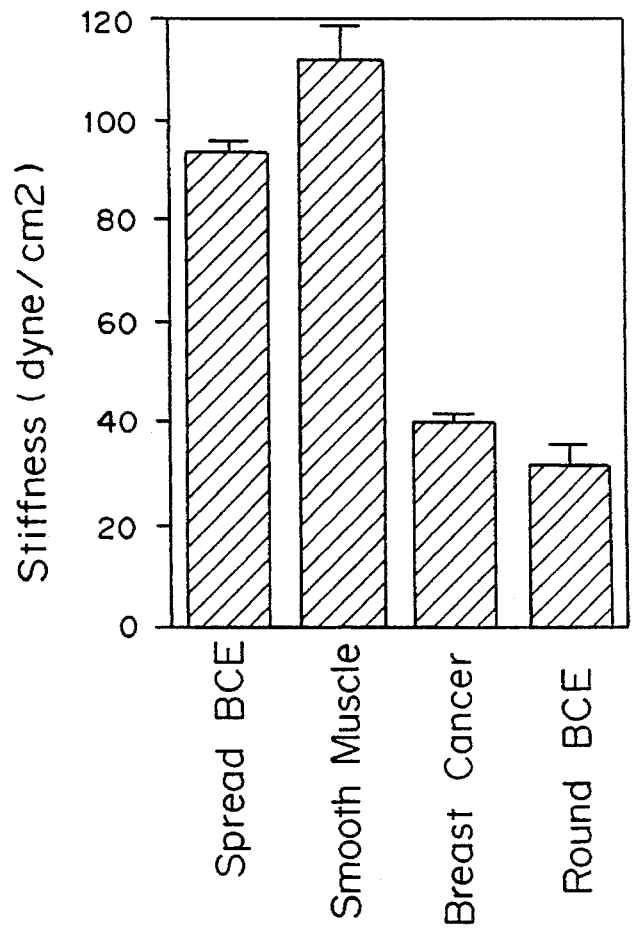
FIG. 7 is a graph of the stiffness (dynes/cm$^2$) for spread bovine capillary endothelial (BCE) cells, bovine pulmonary arterial smooth muscle cells, breast cancer cells, and round BCE.

This is demonstrated by the data in FIG. 7, showing that the stiffness of breast cancer carcinoma cells is much lower than that of endothelial cells when plated at the same concentration of fibronectin (500 ng/ml) and for the same duration (8–10 hours). These results suggest that cancer cells are much floppier than normal cells, that is to say, their cytoskeletal organization is very different from normal cells; actually, stiffness of cancer cells resembles that of round normal cells which are plated on very low density of fibronectin (10 ng/ml).

This example demonstrates that one application for this method is for staging early tumors and pre-malignant lesions, e.g., from biopsy specimens, in terms of their malignant and metastatic potential.

Example 4

Screening for Anti-Tumor Compounds Which Induce Detectable Changes in the Cytoskeleton This technology can also be used to identify new anti-cancer compounds based on their ability to produce a specific cytomechanical response. Measuring changes in the CSK of cells from tumor biopsies can provide a rapid method to characterize tumor cell sensitivity to currently available anti-cancer drugs.

Two compounds were tested for their effect on cells using the method described herein: a potent angiogenesis inhibitor, TNP-470 or AGM-1470, that is currently in Phase I clinical trials for the treatment of solid tumors, and taxol, which is used clinically in the treatment of breast cancer.

Figure 8:
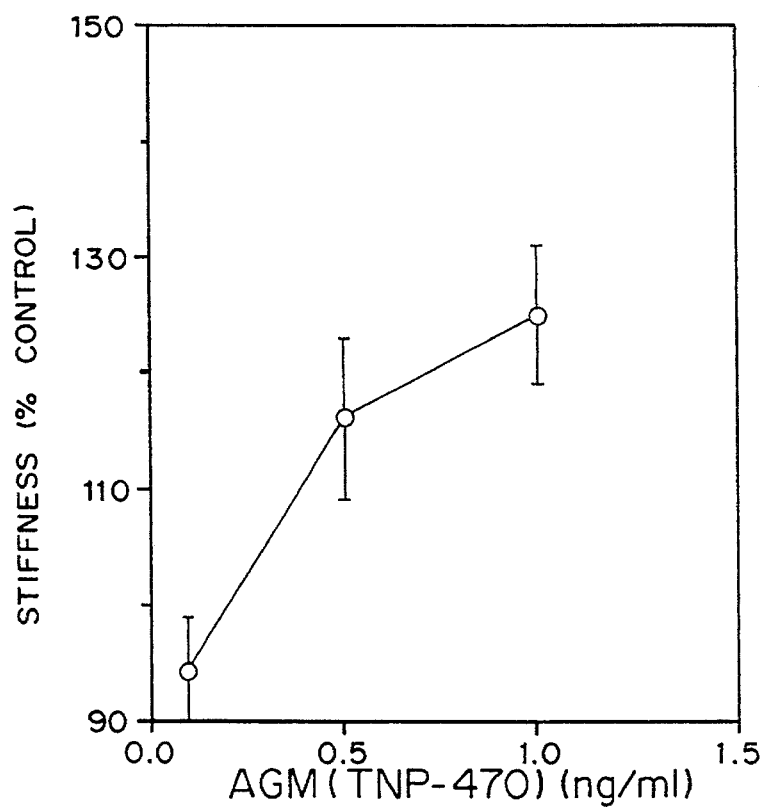
FIG. 8 is a graph showing the stiffness (% of control) for control BCE and BCE treated with TNP-470.

TNP-470 produces a specific change in CSK mechanics in its target, the capillary endothelial cells, as shown by FIG. 8. The shear stiffness of the CSK increased by 30% within 15 minutes after drug addition. The response is dose-dependent response: from 100 pg/ml to 1 ng/ml.

Figure 9A:
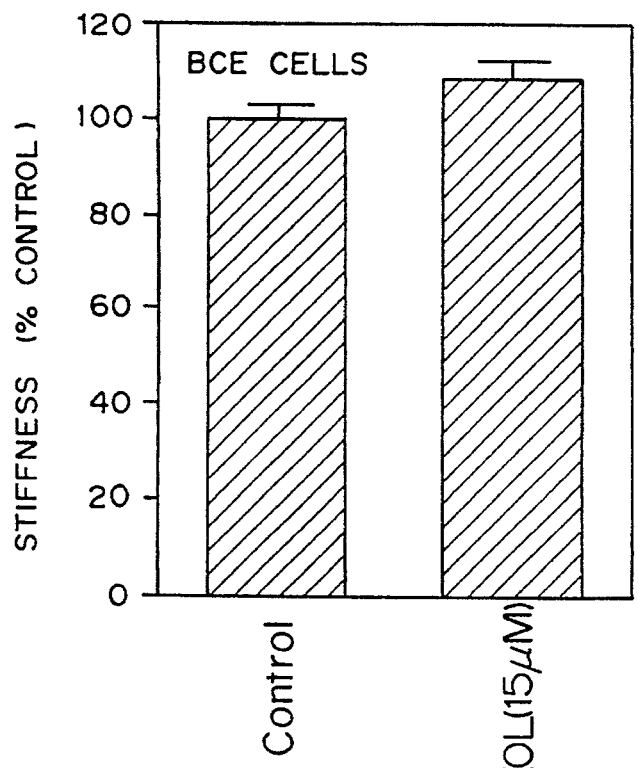
FIGS. 9a and 9b are graphs of the stiffness (% of control) for control BCE and BCE treated with 15 µM taxol (FIG. 9a) and control breast cancer cells and breast cancer cells treated with 15 µM taxol (FIG. 9b).
Figure 9B:
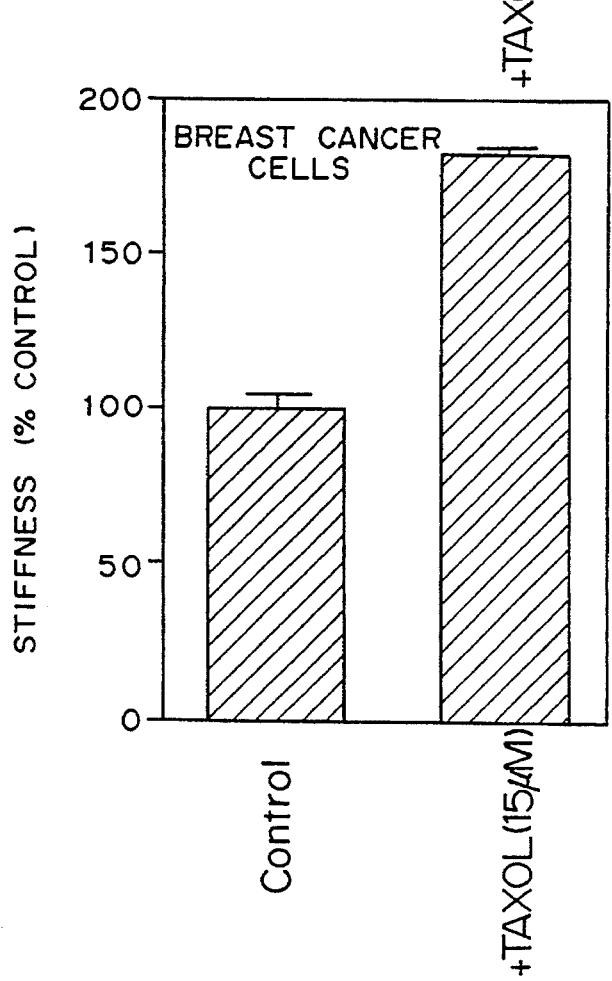

Taxol (15 µM) also increased CSK stiffness of BCE, but only by 10%. In culture, taxol was only about half as effective as TNP-470 at inhibiting the growth of these cells. The effect of taxol was cell type specific, as measured as described herein as percent stiffness of control cells. As shown by FIG. 9a, there was very little effect on BCE; in contrast, as shown by FIG. 9b, there was a significant effect on breast cancer cells. Taxol (15 µM) increased cell stiffness by 80% in cancer cells.

Given that many of the anti-cancer compounds currently in use target the CSK, including taxol and vincristine, this technology seems to be an excellent method for rapid drug screening.

Modifications and variations of the method and system of the present invention will be obvious to those skilled in the art from the foregoing detailed description and are intended to fall within the scope of the appended claims.

We claim:

1. A system for determining the effect of mechanical stimulation of molecules which are present on the surface of cells comprising:

ferromagnetic microbeads having attachment molecules coated thereon which bind to the molecules present on the surface of cells, the microbeads having a diameter between 0.03 and 500 microns, and wherein the attachment molecules are selected from the group consisting of matrix molecules that bind to integrins and molecules that bind to other receptors on the cell surface and physically interconnect with distinct cytoskeletal proteins, wherein the integrins or receptors are the molecules present on the surface of the cells to be tested;

an apparatus for imposing on the microbeads a strong external magnetic field resulting in magnetization and alignment of the magnetic moments of the microbeads and for imposing on the microbeads defined mechanical stresses between zero and 300 dyne/cm$^2$ using a weaker "twisting" magnetic field applied perpendicular to the original field; and a magnetometer to measure the component of the remanent magnetic field vector in the direction of the original magnetization as a function of time.

2. The system of claim 1 wherein the strong external magnetic field is greater than 250 gauss and the weaker twisting magnetic field is between zero and 100 gauss.

3. The system of claim 1 wherein the attachment molecules are selected from the group consisting of fibronectin, vitronectin, collagens, laminin, fibrinogen, fibulin, dystrophin, heparan sulfate proteoglycan, plasminogen activator/urokinase, gangliosides, Von Willebrand's factor, entactin, Echistatin, antibodies to integrins, synthetic RGD containing peptides, cadherins, and lectins.

4. The system of claim 1 wherein the cells are selected from the group consisting of plant cells, animals cells, yeast, and bacteria.

5. The system of claim 2 wherein the cells are living.

6. The system of claim 3 wherein the cells are permeabilized.

7. The system of claim 1 further comprising a compound to be tested for an effect on the molecules present on the surface of cells.

8. An in vitro method for detecting the effect of mechanical stimulation of molecules immobilized on a surface comprising:

mixing ferromagnetic microbeads having coated thereon attachment molecules which bind to the molecules immobilized on a surface, wherein the attachment molecules are selected from the group consisting of matrix molecules that bind to integrins and molecules that bind to other receptors that span the cell surface and physically interconnect with distinct cytoskeletal proteins, the microbeads having a diameter between 0.03 and 500 microns, with the molecules immobilized on a substrate;

treating the mixture of the microbeads and the immobilized molecules with a compound which is to be tested for an effect on the interaction of the attachment molecules on the microbeads with the immobilized molecules;

imposing on the microbeads a strong external magnetic field resulting in magnetization and alignment of the magnetic moments of the microbeads;

imposing on the microbeads defined mechanical stresses between zero and 300 dyne/cm$^2$ using a weaker "twisting" magnetic field applied perpendicular to the original field;

measuring the component of the remanent magnetic field vector in the direction of the original magnetization as a function of time;

comparing the effect of the compound to be tested on the interaction of the immobilized molecules with the attachment molecules on the microbeads with the effect of a compound having a predetermined effect on the interaction of the immobilized molecules with the attachment molecules on the microbeads.

9. The method of claim 8 wherein the strong external magnetic field is greater than 250 gauss and the weaker twisting magnetic field is between zero and 100 gauss.

10. The method of claim 8 wherein the attachment molecules are selected from the group consisting of fibronectin, vitronectin, collagens, laminin, fibrinogen, fibulin, dystrophin, heparan sulfate proteoglycan, plasminogen activator/urokinase, gangliosides, Von Willebrand's factor, entactin, Echistatin, antibodies to integrins, synthetic RGD containing peptides, and cadherins.

11. The method of claim 8 wherein the substrate is cells selected from the group consisting of plant cells, animal cells, yeast, and bacteria.

12. The method of claim 11 wherein the cells are living.

13. The method of claim 11 wherein the cells are permeabilized.

14. The method of claim 8 wherein the molecules are immobilized on a non-cellular substrate.

15. The method of claim 11 further comprising repeating the method using cells of a second type and comparing the effect of the compound to be tested on the interaction of the attachment molecules on the microbeads with the molecules on the surface of the cells which were first tested with the interaction of the attachment molecules on the microbeads with the molecules on the surface of the second type of cells.

16. The method of claim 11 wherein cell functions are altered by the addition of compound.

17. The method of claim 16 wherein the cell function is growth or stiffness.

18. The method of claim 16 wherein the cell function is the production of molecules by the cells which is altered by exposure to the compound to be tested.

19. An in vitro method for detecting the effect of mechanical stimulation of molecules immobilized on cells comprising:

treating the cells with a compound which is to be tested for an effect on the interaction of the molecules immobilized on cells with attachment molecules coated on ferromagnetic microbeads, wherein the attachment molecules bind to the immobilized molecules and are selected from the group consisting of matrix molecules that bind to integrins and molecules that bind to other receptors that span the cell surface and physically interconnect with distinct cytoskeletal proteins, the microbeads having a diameter between 0.03 and 500 microns;

mixing the treated cells with the microbeads;

imposing on the microbeads a strong external magnetic field resulting in magnetization and alignment of the magnetic moments of the microbeads;

imposing on the microbeads defined mechanical stresses between zero and 300 dyne/cm$^2$ using a weaker "twisting" magnetic field applied perpendicular to the original field;

measuring the component of the remanent magnetic field vector in the direction of the original magnetization as a function of time;

comparing the effect of the compound to be tested on the interaction of the immobilized molecules with the attachment molecules on the microbeads with the effect of a compound having a predetermined effect on the interaction of the immobilized molecules with the attachment molecules on the microbeads.

20. An in vitro method for detecting the effect of mechanical stimulation of molecules immobilized on cells comprising:

mixing the cells with ferromagnetic microbeads having coated thereon attachment molecules which bind to the molecules immobilized on the cells, wherein the attachment molecules are selected from the group consisting of matrix molecules that bind to integrins and molecules that bind to other receptors that span the cell surface and physically interconnect with distinct cytoskeletal proteins, the microbeads having a diameter between 0.03 and 500 microns;

imposing on the microbeads a strong external magnetic field resulting in magnetization and alignment of the magnetic moments of the microbeads;

treating the mixture of the cells and the magnetized microbeads with a compound which is to be tested for an effect on the interaction of the molecules immobilized on cells with the attachment molecules on the microbeads;

imposing on the microbeads defined mechanical stresses between zero and 300 dyne/cm$^2$ using a weaker "twisting" magnetic field applied perpendicular to the original field;

measuring the component of the remanent magnetic field vector in the direction of the original magnetization as a function of time;

comparing the effect of the compound to be tested on the interaction of the immobilized molecules with the attachment molecules on the microbeads with the effect of a compound having a predetermined effect on the interaction of the immobilized molecules with the attachment molecules on the microbeads.

21. An in vitro method for detecting the effect of mechanical stimulation of molecules immobilized on cells comprising:

mixing the cells with ferromagnetic microbeads having coated thereon attachment molecules which bind to the molecules immobilized on the cells, and with a compound which is to be tested for an effect on the interaction of the molecules immobilized on the cells with the attachment molecules on the microbeads, wherein the attachment molecules are selected from the group consisting of matrix molecules that bind to integrins and molecules that bind to other receptors that span the cell surface and physically interconnect with distinct cytoskeletal proteins, the microbeads having a diameter between 0.03 and 500 microns;

imposing on the microbeads a strong external magnetic field resulting in magnetization and alignment of the magnetic moments of the microbeads;

imposing on the microbeads defined mechanical stresses between zero and 300 dyne/cm$^2$ using a weaker "twisting" magnetic field applied perpendicular to the original field;

measuring the component of the remanent magnetic field vector in the direction of the original magnetization as a function of time;

comparing the effect of the compound to be tested on the interaction of the immobilized molecules with the attachment molecules on the microbeads with the effect of a compound having a predetermined effect on the interaction of the immobilized molecules with the attachment molecules on the microbeads.

\* \* \* \* \*